United States Patent [19]

Williams

[11] 4,034,746
[45] July 12, 1977

[54] RETRACTOR

[76] Inventor: Robert W. Williams, 3201 S. Maryland Parkway, Las Vegas, Nev. 89109

[21] Appl. No.: 601,059

[22] Filed: Aug. 1, 1975

[51] Int. Cl.$^2$ .......................................... A61B 1/32
[52] U.S. Cl. .................................. 128/17; 128/20; 128/345
[58] Field of Search .......... 128/17, 20, 303 R, 321, 128/341, 345, 346; 81/302, 425 A, 425 R; 29/225, 227

[56] References Cited

U.S. PATENT DOCUMENTS

| | | | |
|---|---|---|---|
| 3,038,467 | 6/1962 | Souatkin | 128/17 |
| 3,470,872 | 10/1969 | Grieshaber | 128/17 |

FOREIGN PATENT DOCUMENTS

| | | | |
|---|---|---|---|
| 511,203 | 3/1920 | France | 128/20 |
| 275,298 | 3/1970 | U.S.S.R. | 128/17 |

Primary Examiner—Robert W. Michell
Assistant Examiner—Henry S. Layton
Attorney, Agent, or Firm—Jerry R. Seiler

[57] ABSTRACT

A surgical retractor of the type having a pair of movable handles pivoted on a common pivot pin or hinge member each handle having an elongated arm extending upwardly therefrom for reciprocal expansion or contraction when the handles are reciprocally moved, the improvement comprising a blade or plate member secured along one end of the first one of the arms opposite a first one of the handles, the plate member being angled inwardly from the elongated arm and directed downwardly approximately normal to a plane through which the arms reciprocally travel during movement, and an elongated rod member secured to one end of the second arm opposite the second handle, the arm extending to a length at least as great as the length or distance along the first arm to the center of the plate member, a rod member extending downwardly along a plane substantially normal to the plane through which the arms reciprocate, and an outwardly extending pointed pin at the end of the rod member opposite the arm.

9 Claims, 4 Drawing Figures

RETRACTOR

BACKGROUND OF THE INVENTION

Surgical retractors for expanding the width of an incision during surgical procedures are known. Such retractors are designed to operate in a scissor like manner and utilize plates or other members which are inserted into the surgical incision. The plates or members are then spread apart utilizing pivotally movable handles thereby spreading or increasing the width across the incision providing the surgeon with sufficient room to carry out the surgical procedure. The present invention is directed to an improved retractor especially designed for the operative procedure of micro-lumbar discectomy in which the incision is relatively small (2cm) thereby necessitating optimum utilization of the rather confined space. In this technique, a right sided herniated lumbar disc will be treated with the surgeon standing on the right side of the patient who is in the face down position. The left sided herniated disc will therefor be treated from the left side of the patient in a similar position. Even though the surgeon's orientation to the patient will remain unchanged, the retractor of the invention shown in the drawings is designed specifically for the right handed surgeon while a mirror image thereof will be used for the left handed surgeon. Thus, design details such as the handles and locking mechanism of the instrument will always be placed away from the dominate hand of the surgeon thereby minimizing any interference of the instrument with the other instruments utilized in the surgeon's dominate hand while carrying out the procedure. Moreover, known retractors have a disadvantage of the instrument arm being often nearest the surgeon and interfering with other instruments, such as forceps used in an operation. Accordingly, the present retractor is designed to optimize the advantages of such a procedure thereby giving the surgeon ample space in which to work and at the same time preventing interference with other instruments as well as the microscopic field of vision.

SUMMARY OF THE INVENTION

The present invention is directed to an improved surgical retractor, especially suited for spinal surgical procedures and more especially a device for the operative procedure of lumbar discectomy. The unique features of the device includes a plate secured adjacent to the end of one of the spreadable arms which plate is angled inwardly for a portion of its length thereby offering the advantage of displacing the arm portion from the microfield when the retractor is open. Another improved feature is that the other (opposite) elongated arm extends a greater length than those previously known instruments of this type whereby it terminates approximately in line with or across from the upper edge of the plate on the opposite arm. In addition, a secondary arm or rod member angles somewhat downwardly from the end of the second arm and terminates in an outwardly projecting point or tip approximately ⅔ of the plate length and centered with respect to the plate width. The combination of the one extended arm and angular plate attached to the other further provides for additional retractability of the instrument to safely maximize the opening of the incision.

DETAILED DESCRIPTION OF THE INVENTION

Figure 1:
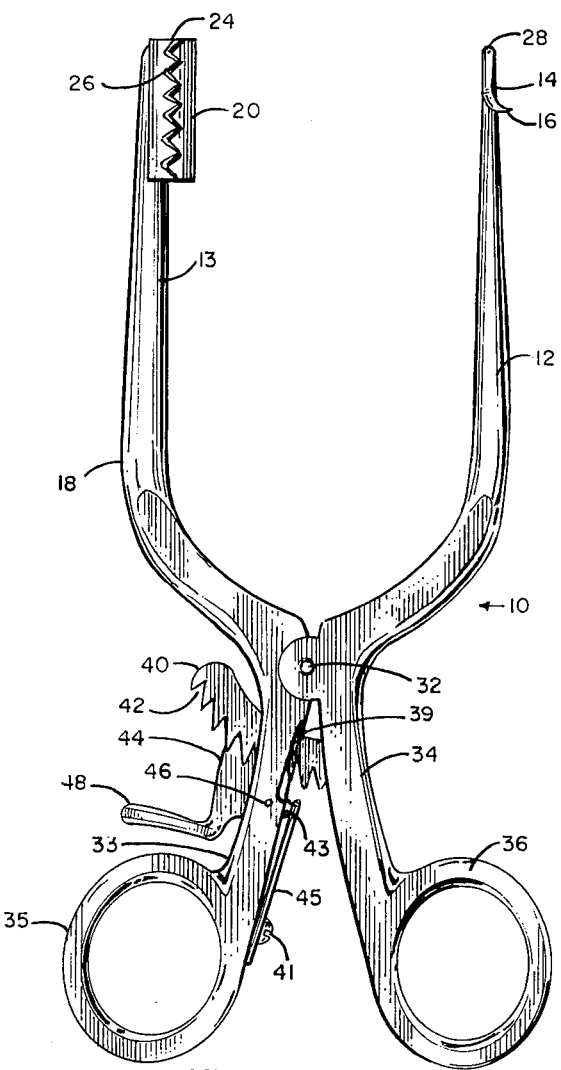
FIG. 1 is a plan view of the retractor of the invention.

FIG. 1 shows a retractor 10 of the invention for use by a right handed surgeon. It is to be understood that a left hand instrument will have the same features but will be a mirror image of that shown and described. The retractor comprises a pair of movable handles 33 and 34 both secured to a common pivot pin 32 which extends through a slot in each of the handles. Thus, the handles are hinged on the pin. At the lower ends of the handles are rings 35 and 36 through which a surgeon or operator may place a thumb and finger for selectively spreading or contracting the handles which concomitantly results in opposite movement of jaw-like arms 12 and 18. Since arm 12 is attached to handle 34 and arm 18 to handle 33, when the handles are contracted, this will cause the arms to be spread, opened or expanded and visa versa.

Figure 2:
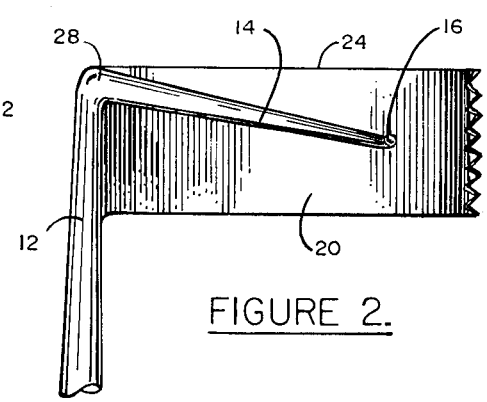
FIG. 2 is a side view of the upper end of the instrument.

Observing further FIG. 2, an arc shaped rack or ratchet member 40 having a plurality of teeth or notches 42 is attached to handle 34. The rack extends through slot 39 in handle 33 so that as handle 34 is moved relative to handle 33, the rack moves freely in slot 39. A pawl member 44, also having a plurality of teeth preferably at least four, for mating with those of the rack is pivotally secured on handle 33 by pin 46 which extends through the handle and pawl. A flattened projection or flange 48 provides a surface against which the operator may press to rotate the pawl thereby disengaging the pawl teeth from those of the rack. Preferably, the pawl will also include a projection or knob 43 which extends through the other end of slot 39 in arm 33. A leaf spring 45 is attached at one end by rivet or screw 41 to arm 33 and abuts pawl projection 43 thereby biasing the pawl in the upward position for engagement or mesh of its teeth with those of rack 40. With the pawl normally biased upwardly and urged against the rack to set the arm spread until the operator depresses flange 48 disengaging it from the rack thereby allowing movement of the handles. Moreover, preferably the teeth in the rack are slanted so that the handles may be moved toward one another thereby spreading the arms without requiring depression of tab 48 but not visa versa, i.e., spreading of the handles first requires depression of the finger tab to disengage the pawl teeth from the rack. The depth of the teeth in both the rack and pawl are about 3mm deep or more in order to give greater stability and reduce the risk of slippage once the retractor has been expanded in the incision during surgery.

Figure 3:
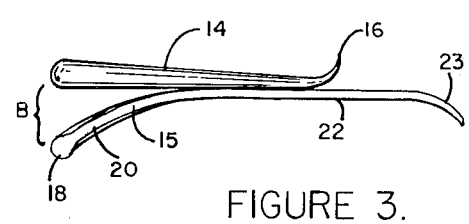
FIG. 3 is an end view of the plate and rod member in a closed position.

FIG. 1 illustrates the retractor 10 from the underside, the device shown normally to be used by a right handed surgeon whereby plate 20 and rod 14 extend into the incision with the plate nearest the surgeon with the handles being operated by the surgeon's non-dominant or left hand. Thus, with the plate and rod of the device extending into the incision as illustrated in FIG. 3, the surgeon will work into the surgical area with his right hand between plate 20 and rod 14, the handles of the instrument being directed away from the surgeon's right hand.

Observing now all four Figures, attached to and extending from upper end portion of arm 18 is an angular plate 20. The lower portion of both arms 12 and 18 are curved or angled to converge at the common pivot 32.

Plate 20 is rather thin in cross-section and terminates in a toothed end surface 26 which teeth extend substantially along the botom plate edge. The plate extends downwardly when both arms 12 and 18 lie along a horizontal plane as the instrument is used as illustrated in FIG. 3. Observing particularly FIGS. 1 and 3, plate 20 is secured along the upper end of arm 18 at a side edge opposite the toothed end 22 and comprises an angled portion 15 directed inwardly toward rod 14, a straight portion 22 which lies approximately parallel to rod 14, and an end portion 23 angled outwardly away from rod 14 and along the edge of which are located the teeth. The relative lengths and angles of the plate portions are somwhat critical, especially in a micro lumbar discectomy instrument since the rod and plate must meet when the instrument is closed for insertion into the incision. Accordingly, the overall length of plate 20 is at least five cm and preferably between 5 and about 9 cm and the width about 2 cm or less to about 1 cm. Moveover, the length of angled portion 15 of plate 20 is preferably between about 0.5 and 2.5 cm and more preferably 1 to 2 cm so that the distance B between the inner plate edge and the end at arm 18 is about 1 1 cm. Observing also FIG. 4, this one cm plate angle will allow the surgeon to insert an instrument such as forceps into the incision 40 over the upper side or arm 18 which is seen to be held away from the inner edge of the incision when the retractor is open as shown. The angle of plate portion 15 relative to plate portion 22 will preferably be between about 20° and about 45°, the specific angle being within this range to achieve the 1 cm distance B. The specific angle of end portion 23 is preferably between about 25° and 45°, sufficient to expose teeth 26 for properly gripping the flesh in the incision to stabilize the instrument. Thus, this important feature substantially eliminates interference of the arm with the surgeon's field of view as well as minimizing its interference with other instruments used from that side of the patient where the surgeon is working during the procedure. It will be understood that the angles given for the plate portions referred to are nominal since the actual surfaces will generally be curved rather than forming abrupt angles relative to flat plate portion 22.

Figure 4:
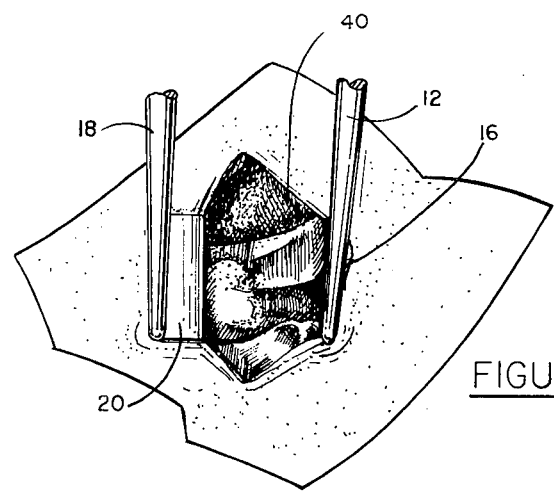
FIG. 4 is a top view illustrating the disposition of retractor components in use to spread the sides of an incision.

The other or opposite arm 12 is secured at its lower end and is integral with handle 34. The major portion of arm 12 is elongated and extends substantially straight up to its terminal end 28 to which rod or extension portion 14 is connected. The upper end 28 of arm 12 preferably extends to at least a length equivalent to and across from the mid point or center of the width of plate 20 and more preferably extends to a distance across from the upper edge 24 of plate 20 as illustrated. Rod 14 extends normal to the arm and substantially parallel with plate 20 and also angles downwardly from the upper arm end so that it terminates in a pointed projection 16 at approximately the mid point or center of plate 20. Moveover, the length of the rod is preferably between about two-thirds and the full length of plate 20 so that pointed projection 16 is at about the center of the plate width and at least two-thirds of its length. With such a features, when the device is used, with rod 14 extending into the incision, because of the length of arm 12, the side of the rod will lie across from the top of plate 20 and then extend slightly downwardly so that point 16 is approximately mid-width of the plate as shown in FIGS. 2 and 4. Further, point 16 projects outwardly substantially at 90° or normal to the elongaged axis of the major portion of arm 12. Within the incision the point will then extend into the spinal ligaments well away from the nerves thereby stabilizing the instrument once it has been properly placed and expanded, but preventing injury to the nerve elements by its relative shorter length. Accordingly, the length of rod 14 is preferably between about 3 and about 8 cm, again, depending on the length of plate 20 and terminating at about two-thirds of the plate length. For a plate length of 5 cm, rod length will be about 3.3 cm as shown to approximate scale in FIGS. 2 and 3. The rod length is important to prevent hook or projection 16 from being driven into the neural canal as it would if the rod was substantially longer, approaching the length of plate 20. On the other hand, if rod 14 is too short, the projection would simply rest on bone, thereby often producing torque forces which would minimize the stability of the instrument.

Again, use of the device is illustrated in FIG. 4, the plate and rod extending into incision 40. Handles 33 and 34 (FIG. 1) are brought together as needed to spread arms 12 and 18 and open incision to the desired extend. The unique features of the instrument make it especially useful for microsurgical techniques, where maximum utilization of small incisions as well as field of view are absolute requirements for success in these procedures. Moveover, as previously explained, the device shown is for use by a right handed surgeon in a micro lumbar discectomy, with the plate being on the right side of the patient (face down) and the surgeon working from the right side of the patient. With the plate and rod extending into the incision, the instrument handles are directed to the surgeon's left. An instrument for use by a left handed surgeon will be a mirror image of that shown. Other modifications within the purview of the invention to achieve the advantages thereof will be evident to those skilled in the art.

I claim:

1. A retractor having a pair of arms being movable about a common pivot member and along a common plane,
    the first arm of said pair having a handle secured at a first end and a rod member secured at a second opposite end thereof, said rod extending along a plane substantially normal to the common arm movement plane, and a pointed tip member at the end of said rod member said tip member directed away from a plate member and substantially parallel to the common arm movement plane,
    the second arm of said pair having a handle secured at a first end and a plate member secured at a second opposite end thereof, said plate member having a first portion extending toward said rod member at an angle from said second arm, a second portion extending along a plane substantially parallel with said rod member and along a plane nominally normal to said common arm movement plane and a toothed edge opposite said second arm which edge is directed angularly away from said rod member.

2. The retractor of claim 1 wherein the distance from said pivot member to the intersection of said rod member and said first arm is at least equal to the distance between said pivot member and the middle of said plate member along said second arm.

3. The retractor of claim 2 wherein the second plate portion is offset inwardly between 0.5 and 1.5 cm from an axis along said second arm.

4. The retractor of claim 3 wherein said offset distance is about 1 cm.

5. The retractor of claim 4 wherein the plate has a width of between 1 and 2 cm.

6. The retractor of claim 3 wherein said plate has a length of between 5 and 9 cm.

7. The retractor of claim 3 wherein the length of said rod is about ⅔ the length of said plate.

8. The retractor of claim 1 wherein the distance from said pivot member to the intersection of said rod member and said first arm is greater than the distance between said pivot member and the midway point of said plate member along said second arm.

9. The retractor of claim 1 wherein the angle between said first plate portion and said second portion is between 20° and 45°.

* * * * *